(12) United States Patent
Buchner et al.

(10) Patent No.: US 8,422,413 B2
(45) Date of Patent: Apr. 16, 2013

(54) PROCESS AND DEVICE FOR THE WIRELESS TRANSMISSION OF DENTAL PROCESS DATA

(75) Inventors: Kerstin Buchner, Heppenheim (DE); Thomas Ertl, Dreieich (DE); Wigbert Hauner, Langen (DE)

(73) Assignee: DENTSPLY International Inc., York, PA (US)

( * ) Notice: Subject to any disclaimer, the term of this patent is extended or adjusted under 35 U.S.C. 154(b) by 1598 days.

(21) Appl. No.: 11/811,258

(22) Filed: Jun. 8, 2007

(65) Prior Publication Data

US 2008/0031150 A1    Feb. 7, 2008

Related U.S. Application Data

(63) Continuation of application No. 10/665,787, filed on Sep. 18, 2003, now abandoned.

(51) Int. Cl.
*H04B 7/00*    (2006.01)

(52) U.S. Cl.
USPC ............................................ 370/310; 370/537

(58) Field of Classification Search .......... 370/535–537, 370/310, 328
See application file for complete search history.

(56) References Cited

U.S. PATENT DOCUMENTS

| | | | | | |
|---|---|---|---|---|---|
| 3,846,588 | A | * | 11/1974 | Holzwarth | 370/492 |
| 4,723,237 | A | * | 2/1988 | Andrew et al. | 370/204 |
| 4,738,133 | A | * | 4/1988 | Breckel et al. | 73/114.58 |
| 5,509,013 | A | * | 4/1996 | Adachi et al. | 370/538 |
| 5,754,111 | A | * | 5/1998 | Garcia | 340/573.1 |
| 7,046,701 | B2 | * | 5/2006 | Mohseni et al. | 370/537 |
| 7,158,845 | B2 | * | 1/2007 | Parsons et al. | 700/96 |
| 2001/0023056 | A1 | * | 9/2001 | Grunenfelder et al. | 433/27 |

FOREIGN PATENT DOCUMENTS
WO    WO 02/076330    10/2002

* cited by examiner

*Primary Examiner* — Ajit Patel
(74) *Attorney, Agent, or Firm* — David A. Zdurne; Douglas J. Hura; Leana Levin

(57) ABSTRACT

A dental apparatus and process for the transmission of dental data by means of a transmitter and a receiver in a wireless manner.

18 Claims, 1 Drawing Sheet

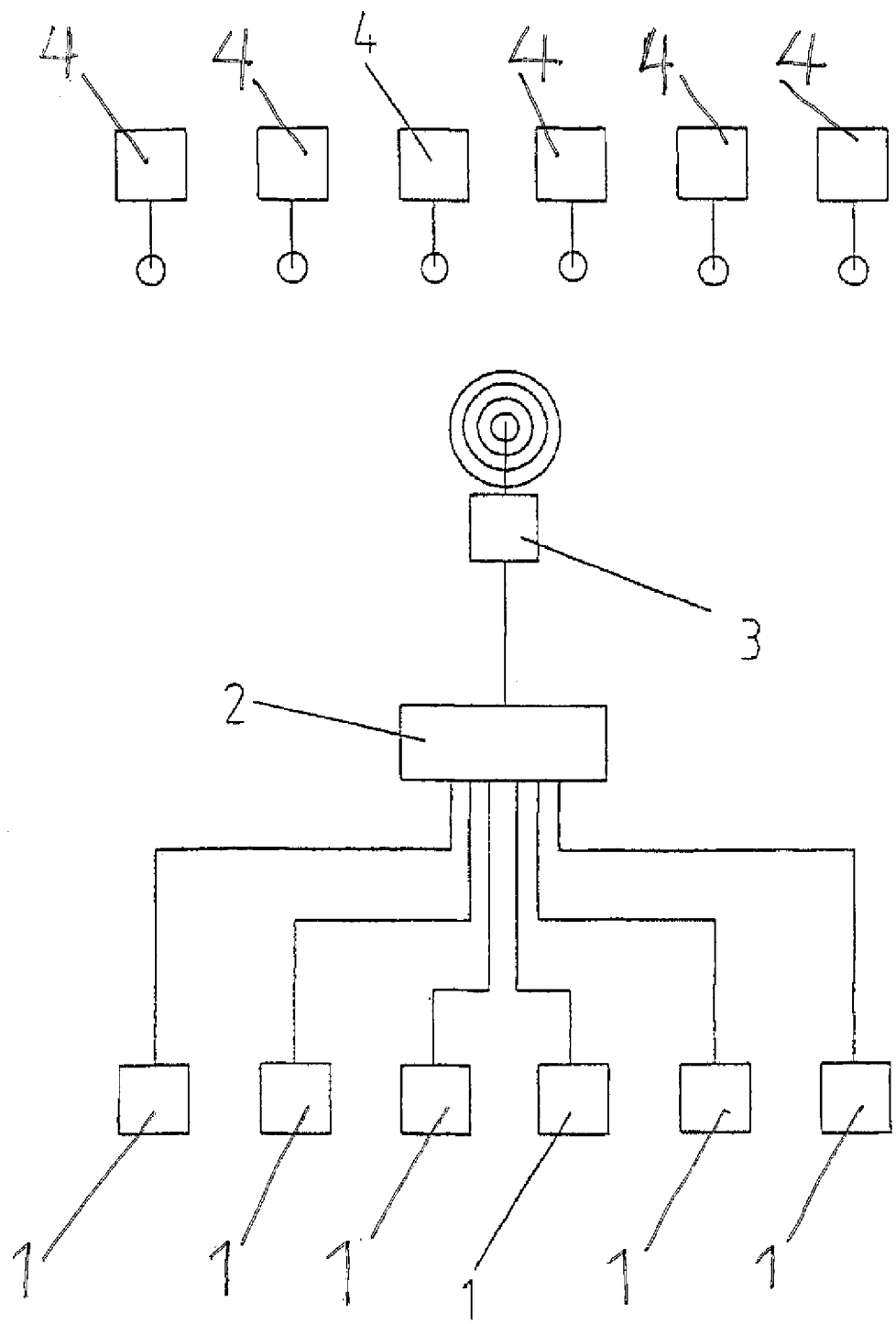

PROCESS AND DEVICE FOR THE WIRELESS TRANSMISSION OF DENTAL PROCESS DATA

CLAIM OF PRIORITY

The present invention is a continuation application of U.S. patent application Ser. No. 10/665,787, filed on Sep. 18, 2003, now abandoned, which claims the benefit of priority to international application Ser. No. PCT/EP02/03138, filed on Mar. 20, 2002, and foreign application Ser. No. DE10113753.2, filed Mar. 21, 2001, which are herein incorporated by reference for all purposes.

CROSS-REFERENCE TO RELATED APPLICATIONS

This patent application claims the benefit of and priority to U.S. application Ser. No. 10/665,787, filed on Sep. 18, 2003, which is herein incorporated by reference for all purposes.

BACKGROUND OF THE INVENTION

1. Field of the Invention

The invention concerns a process for the wireless transmission of process data in a dental laboratory by means of a stationary transmitter and a portable receiver. In particular, the process data come from dental apparatuses, such as, for example, a firing kiln. The present invention also concerns a system for carrying out the process.

2. Brief Description of the Related Art

Several production processes are usually operated in a dental laboratory at the same time by one dental technician. For this purpose, a dental laboratory usually has several work stations, which can be utilized by a dental technician for carrying out individual production steps. Operated at the work stations are typically firing kilns, wax melting apparatuses, composite photocuring apparatuses, electroplating apparatuses, steam jets, sterilization equipment, casting apparatuses, preheating ovens, thorough firing ovens, pressing ovens, or CAD/CAM milling apparatuses. To an increasing extent, these apparatuses permit a process to be conducted automatically, so that the physical presence of the dental technician at the work station during the automated phases can be dispensed with. During this time, the dental technician can dedicate himself to a parallel production process at a different work station. However, it is often necessary for the dental technician to monitor the automated operation in order to intervene in the process in the event of problems or in order to continue the production process. To this end, it is necessary for the dental technician to check the process data of work stations. Depending on the organization and size of a dental laboratory, it can happen that the individual work stations that the dental technician utilizes when carrying out several production processes in parallel cannot be monitored in a straightforward manner without the necessity of visiting the work station to be monitored.

The means of presenting process data in the dental laboratory, particularly in the case of vacuum kilns, has been known for a long time. In terms of design, they consist essentially of photodiodes and alphanumeric or graphical display screens and are connected directly to the vacuum kilns as an integral component of the control. Large displays are used in order to make the process data easier to perceive from a relatively long distance. Also known is the display of the process data that is most important for the operator at the highest point of the kiln by means of displays.

A drawback in all of these solutions is the fact that the operator always has to have visual contact with the apparatus in order to perceive the current process data. In the case that visual contact is not possible, because the dental technician is present at another work station, the dental technician has to establish visual contact by moving to the work station to be monitored. In this way, valuable work time of the dental technician is consumed on the paths between the work stations. Furthermore, it can occur that the monitoring makes it necessary for the dental technician to move so often to the work station to be monitored that the parallel performance of another operating step in another production process is prevented. Finally, it can occur that the dental technician does not recognize in time that an intervention in an automated process is necessary on his part, because he is not able to establish visual contact with the work station to be monitored in a timely manner. During the monitoring, therefore, the strived-for parallel performance of several production processes in the dental laboratory is impaired so much by the necessary visual contact with the apparatus to be monitored that only a small number of production processes can be operated in parallel by an individual dental technician.

Therefore, the object of the invention is to provide a process that makes it possible for the dental technician to carry out a large number of parallel production processes in a rational and reliable manner, with a monitoring of several work stations being possible even when the dental technician does not have the display devices of these apparatuses in view.

Furthermore, the object of the invention is to provide a system that is suitable for carrying out the process in accordance with the invention.

The invention solves the objects indicated by way of a process and a system or device that exhibit the characteristics of the claims.

SUMMARY OF THE INVENTION

The present invention refers to a process for the transmission of process data over a relatively long distance, the process data being transmitted by means of a transmitter and a receiver in a wireless manner. The process data involve data that are produced by dental apparatuses. Typical dental apparatuses are firing kilns, wax melting apparatuses, composite photocuring apparatuses, electroplating apparatuses, steam jets, sterilization equipment, casting apparatuses, preheating ovens, thorough firing kilns, pressing ovens, or CAD/CAM milling apparatuses. The process data concern parameters that are required or are at least appropriate for monitoring by the dental technician. These process data can be such data that the dental technician can also retrieve by means of a conventional output device that is integrated into the apparatus. Beyond this, however, it is also possible to transmit further data that are of use especially when visual contact with the apparatus is absent. Thus, the identity of the operator of the apparatus can be requested or details regarding the object being processed, all the way to data that are made available to the work station from a database via a network. Preferably, the process data involve at least two parameters, which describe the status of the process at a given point in time.

BRIEF DESCRIPTION OF THE DRAWINGS

FIG. 1 illustrates a process for wireless transmission of process data.

DETAILED DESCRIPTION OF THE PREFERRED EMBODIMENTS

Typical process data of a kiln are the baking temperature, the baking time, the level of vacuum, the running time still remaining, the program time, the baking time still remaining, and the programmed temperature program as well as data that concern the object to be baked.

The transmitter is connected to the dental apparatus. In one embodiment, each dental apparatus contains its own transmitter. In a preferred embodiment, a dental apparatus is connected to an external transmitter, which transmits data from several dental apparatuses. In an especially preferred embodiment, there is provided a central transmitting unit that permits the connection of up to six apparatuses, preferably kilns.

This transmitter is preferably stationary. It is advantageous for the connection of the apparatuses to the central transmitting unit to occur with standard cables—for example, RJ45 cables—through an appropriate interface of the apparatus. The process data can be fed to the transmitter either directly or via a data switch. The data switch, as a special multiplexer, can also be an integral component of the transmitter. For example, the central transmitting unit has several inputs, each input being assigned to a fixed address. When the electrical power supply is switched on, the transmitting unit cyclically checks all connections for the presence of an apparatus. Afterwards, the process data of each identified apparatus is retrieved cyclically by the central transmitting unit with a timeout that can be, for example, 80 ms. The length of a cycle can lie in the range of 100 ms to 1 min. The data transmitted by the apparatus are stored in the central transmitting unit. The stored data are subsequently read out from the memory and transmitted in a data frame via the wireless path. It is advantageous for the process data for each parameter to be transmitted through a constant data quantity in each case—for example, 2 bytes. The process data are transmitted in a wireless manner from the transmitter to a receiver. The transmitter sends out a signal that, in terms of the frequency band utilized, is not subject to any special restrictions. However, it has proven advantageous when the transmitter uses an ISM band, such as, for example, one with a frequency of 433.92 MHz. The latter is especially preferred when the transmitter is a so-called low power device (LPD) that has a transmitting power of at most 12 mW. It has been found that this transmitting power is suitable in combination with the frequency used for transmitting data reliably over relatively long distances, even under adverse conditions such as those to be encountered in large dental laboratories.

The signal sent out by the transmitter is received by a radio receiver. In a preferred embodiment, the receiver can be selected beforehand through a special coding of the signals. The selection can occur in an advantageous manner at the dental apparatus. However, it is also possible to set the selection at the central transmitting unit or at the receiver. It is also possible for data to be transmitted to more than one receiver. In this way, it is possible for several dental technicians to be informed via the process data at the same time. In addition, it is possible in this way to incorporate the dental apparatus into a central quality assurance system that collects, saves, and analyzes all process data.

The receiver is supplied with electrical power preferably from a mobile power source, such as a battery or a rechargeable battery, so that the receiver can be worn by the dental technician. The receiver can be activated or deactivated by pressing a button. In a preferred embodiment, the receiver switches off once no data intended for the special transmitter have been received during a time of, for example 1.5 min, which can be set. Whenever the receiver receives data that are intended for it, these data are stored by the receiver. In each case, the receiver stores one set of process data for several parameters, which represent the status of the dental apparatus at a specific point in time. These data are emitted through the transmitter to all receivers immediately after they are received. The display involves, in an advantageous manner, a fully graphical display, which presents the process data in appropriate form. It is possible to display the data simultaneously. However, it is preferred that the dental technician selects the desired parameters and that the process data fitting these parameters are subsequently shown on the display.

The advantages of this process and of the device in accordance with the invention are essentially to be seen in the fact that, by means of a stationary transmitter (3) connected with the kiln (1), the informative process data of a running program are transmitted in a wireless manner to a portable receiver (4) and thus the operator no longer needs necessarily to have visual contact with the apparatus, in order to obtain the desired information.

In an advantageous manner, several furnaces or dental apparatuses can be connected to the transmitter (3) via a data switch (2) in order to use the receiver to retrieve the process data with the portable receiver in a successive and specific manner or to present it selectively. In the case of apparatuses that are operated by several operating personnel, it is preferably also possible to employ several portable receivers (4), with the individual apparatus and the corresponding receiver being assigned to each other through addresses that can be preselected.

Depending on the design of the transmitter and receiver, the range of the wireless transmission of process data lies in the range of up to several kilometers, but preferably up to approximately 30 m in the dental laboratory setting.

FIG. 1 depicts the process for wireless transmission of process data. According to FIG. 1, the device in accordance with the invention involves a system consisting of a transmitter (3) and at least one receiver (4). The transmitter and the receiver are not connected with each other via a cable connection. The transmitter (3) is connected to a data switch (2). The transmitter (3) and the data switch (2) are preferably contained in the same housing of a central transmitting unit. It is possible to connect preferably up to six apparatuses to the central transmitting unit. The data switch contains an electronic control that is connected to the apparatus inputs. The electronic control, on the other hand, is connected to a transmitting unit and set in such a way that the transmitter can transmit the process data of up to six apparatus in a sequential manner. Preferably, the transmitter is chosen in such a way that the process data can be transmitted over a relatively long distance. In particular, it is possible for the apparatuses producing the process data to be assigned individually to different receivers.

The receiver of a device in accordance with the invention includes an antenna for receiving the process data transmitted by the transmitter. The antenna is connected to an electronic control that can store the process data received and process it. The electronic control is connected, on one side, to a display controller. The display controller is connected to a display. The display controller is advantageously an LCD controller that is connected to an LCD module. The electronic control is suitable for processing the process data. It is preferred when the dental technician can influence the processing of the process data by means of a possible input. For example, the dental technician can select a specific parameter or a specific apparatus via an input, so that the electronic control conveys the process data belonging to this parameter or apparatus to the display controller in an appropriate form, so that the selected data appear in the display.

In accordance with the invention, each suitable dental apparatus can be connected with the central transmitting unit in a dental laboratory. The dental technician carries a receiver and can assign this to one or more dental apparatuses. For the case when a dental apparatus, which is assigned to the dental technician's receiver, transmits data through the central transmitting unit, the dental technician can receive these data by means of his receiver and call them up on the display of the receiver. Because input is made possible on the receiver, the dental technician is in the position of selecting the data that are relevant to him from the process data stored in his receiver and of retrieving these data without establishing visual contact with the apparatus display.

The invention claimed is:

1. A process comprising the steps of:
   transmitting process data from a plurality of dental devices over a long distance, wherein the process data from the plurality of dental devices is transmitted by means of a data switch to a transmitter;
   wirelessly sending the process data to one or more receivers; and
   retrieving the process data from the receiver that was received in a wireless manner;
   wherein the process data involve at least two parameters selected from the group consisting of the identity of the operator of the plurality of dental devices, details regarding an object being processed by the plurality of dental devices, current internal temperature of the plurality of dental devices, lapsed operating time of an overall process of the plurality of dental devices, lapsed operating time of a particular process step of the plurality of dental devices, remaining operating time of the overall process of the plurality of dental devices, remaining operating time of the particular process step of the plurality of dental devices, internal pressure and/or vacuum level of the plurality of dental devices, and a programmed temperature program, which describe the status of the process at a given point in time.

2. The process according to claim 1, wherein the process data come from a dental apparatus, which is a firing kiln.

3. A system of carrying out the process for the transmission of process data according to claim 1, wherein the system comprises the following components:
   (a) a transmitter, which can transmit the process data of up to 6 dental apparatuses in a sequential manner;
   (b) one or more portable receivers; and
   (c) a data switch, which receives the process data from at least one of the up to 6 dental apparatuses and transmits the process data to the transmitter.

4. The system according to claim 3, further comprising (d) a dental apparatus that is suitable for acting together with the transmitter in order to transmit process data to a receiver in a wireless manner.

5. The process according to claim 1, wherein the transmitter is a stationary transmitter and a receiver is portable.

6. The process according to claim 1, wherein the process data correspond to a running program of at least one of the plurality of dental devices.

7. The process according to claim 1, wherein multiple portable receivers are provided and each individual dental device and each receiver can be assigned to one another through preselectable addresses.

8. The process according to claim 1, wherein the retrieving step, process data received by the receiver is selectively retrieved by an operator of the receiver.

9. The process according to claim 1, wherein:
   b) the process data correspond to a running program of at least one of the plurality of dental devices; and
   c) the retrieving step, process data received by the receiver is selectively retrieved by an operator of the receiver.

10. The process according to claim 9, wherein:
    a) the process data come from a dental apparatus, which is a firing kiln;
    b) the transmitter is a stationary transmitter and a receiver is portable; and
    c) multiple portable receivers are provided and each individual dental device and each receiver can be assigned to one another through preselectable addresses.

11. The process according to claim 1, wherein:
    b) the process data correspond to a running program of at least one of the plurality of dental devices; and
    c) the retrieving step, process data received by the receiver is selectively retrieved by an operator of the receiver.

12. The process according to claim 11, wherein:
    a) the process data come from a dental apparatus, which is a firing kiln;
    b) the transmitter is a stationary transmitter and a receiver is portable; and
    c) multiple portable receivers are provided and each individual dental device and each receiver can be assigned to one another through preselectable addresses.

13. The system according to claim 3, wherein the transmitter is a stationary transmitter and a receiver is portable.

14. The system according to claim 3, wherein the process data correspond to a running program of at least one of the up to 6 dental apparatuses.

15. The system according to claim 3, wherein the up to 6 dental apparatuses are provided and each individual dental device and each receiver can be assigned to one another through preselectable addresses.

16. The system according to claim 3, wherein:
    b) the process data correspond to a running program of at least one of the up to 6 dental apparatuses; and
    c) process data received by the receiver is selectively retrieved by an operator of the receiver.

17. The system according to claim 16, wherein:
    a) the process data come from a dental apparatus, which is a firing kiln;
    b) the transmitter is a stationary transmitter and a receiver is portable; and
    c) multiple portable receivers are provided and each individual dental device and each receiver can be assigned to one another through preselectable addresses.

18. The system according to claim 16, wherein the up to 6 dental apparatuses includes at least two dental apparatuses.

* * * * *